US00PP12011P2

(12) United States Plant Patent
Gerawan

(10) Patent No.: US PP12,011 P2
(45) Date of Patent: Jul. 24, 2001

(54) NECTARINE TREE NAMED 'PRIMA DIAMOND 19'

(76) Inventor: Michael R. Gerawan, 21249 East Jefferson, Reedley, CA (US) 93654

( * ) Notice: Subject to any disclaimer, the term of this patent is extended or adjusted under 35 U.S.C. 154(b) by 0 days.

(21) Appl. No.: 09/263,365

(22) Filed: Mar. 5, 1999

(51) Int. Cl.[7] ..... A01H 5/00
(52) U.S. Cl. ..... Plt./190
(58) Field of Search ..... Plt./190, 187, 191

*Primary Examiner*—Bruce R. Campell
*Assistant Examiner*—Kent L. Bell

(74) *Attorney, Agent, or Firm*—Townsend and Townsend and Crew

(57) ABSTRACT

'Prima Diamond 19' produces large fruits that mature approximately mid-July in the San Joaquin Valley of Central California. The fruit being approximately similar to 'Summer Fire' (U.S. Plant Pat. No. 7,506) and 'July Red' (U.S. Plant Pat. No. 5,663) in date of maturation. However, the new variety distinguishes from 'Summer Fire' and 'July Red' in numerous respects including the fruit having more exterior red blush color, smoother blemish-free skin surface, lower susceptibility to brown rot, sweeter, fuller flavor and longer post-harvest life. In addition, the tree produces consistently higher levels of production than 'Summer Fire' and 'July Red'.

1 Drawing Sheet

DESCRIPTION

Figure 1:
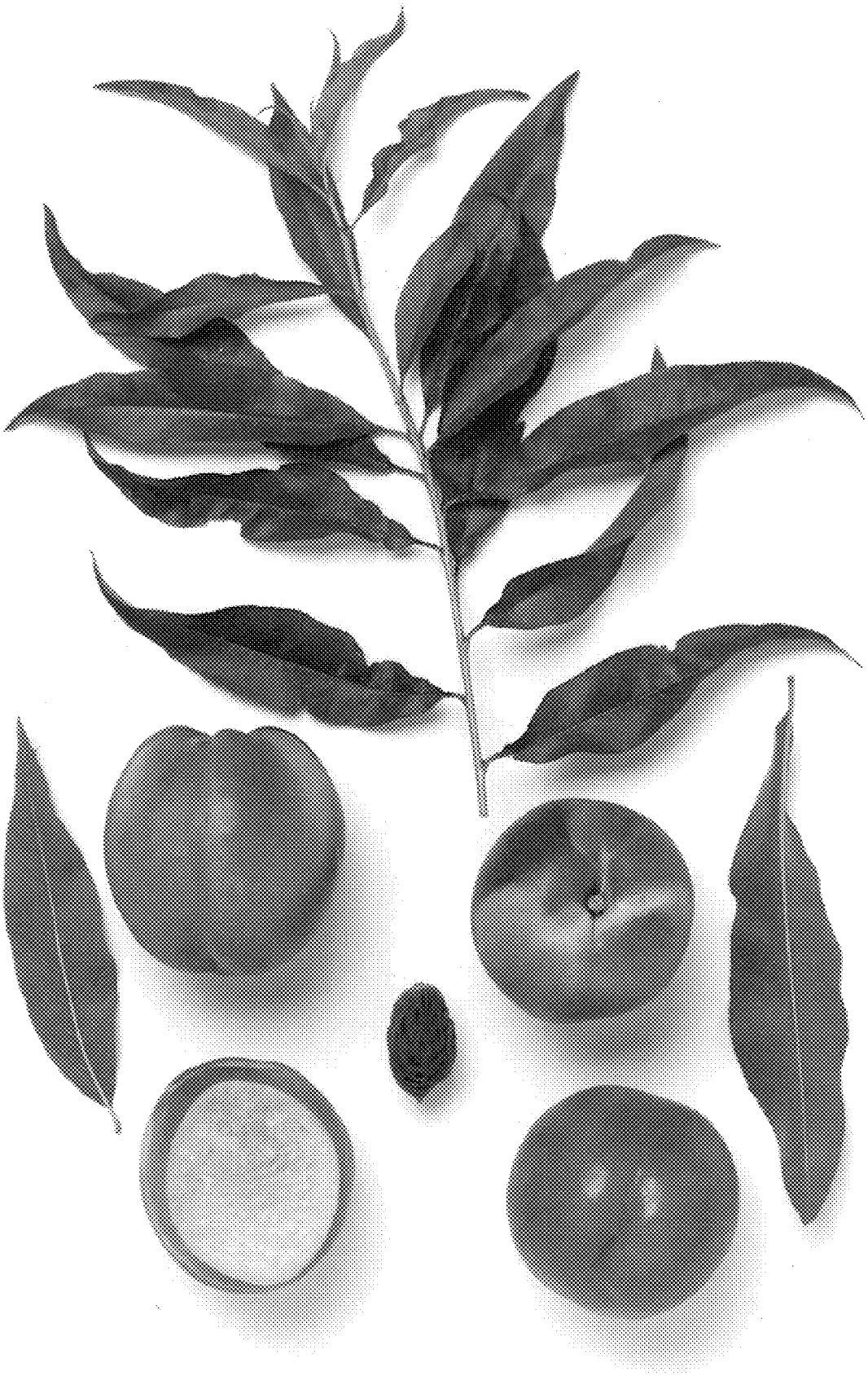

This invention relates to a new and distinct variety of nectarine tree named 'Prima Diamond 19'. The variety is botanically identified as *Prunus persica* var. *nectarina.*

The variety was discovered as a seedling growing in a seed population collected from a planting of mixed commercial nectarine varieties. This seed population was open-pollinated, thus male and female parents are unknown. The seedling was raised by the inventor and was reproduced asexually by him near Sanger in the San Joaquin Valley of Central California by budding onto 'Nemaguard' (non-patented) root stock. The asexually reproduced nectarine trees of the new variety have been continually observed since their reproduction and have been confirmed that they are identical in all respects to the initially discovered tree.

'Prima Diamond 19' produces clingstone fruits that mature for commercial harvesting approximately mid-July in the San Joaquin Valley of Central California. Other commercial nectarine varieties such 'July Red' (U.S. Plant Pat. No. 5,663) and 'Summer Fire' (U.S. Plant Pat. No. 7,506) are also available in mid-July. 'Prima Diamond 19' exhibits characteristics that are superior to these varieties. 'Prima Diamond 19' has more external red skin color and is more consistently productive from year to year. 'Prima Diamond 19' fruits are less susceptible to brown rot and have a longer post-harvest life than 'July Red' and 'Summer Fire'.

'Prima Diamond 19' will hereinafter be described in greater detail.

CHARACTERISTICS

'Prima Diamond 19' is characterized by producing very large, high quality, cling stone fruits which have bright red coloration. This new nectarine variety ripens for commercial harvest in mid-July. Seasonal first harvest dates in the San Joaquin Valley have varied from July 11 to July 27 with the average date of July 19. The average number of days from full bloom to first harvest is 133 days. The average length of time from first pick to final pick is 17 days.

'Prima Diamond 19' nectarine fruits mature in the same time period as 'July Red' and 'Summer Fire' but it distinguishable from those varieties in the following respects:

(1) The exterior red blush color on the fruits is brighter and covers a larger area, (2) The skin is russet-free resulting in a smoother external appearance, (3) The fruit is relatively less susceptible to brown rot, (4) The fruits are highly flavorful resulting in higher consumer acceptance, and (5) The fruits have good external and internal substance for 35 days when stored at 32° F. and 95% relative humidity.

IN THE DRAWING

FIG. 1: Is a color photograph showing mature fruit of the new variety including a top plan view of the fruit with the stem present at the base end (center right); the side elevation of fruit showing the suture thereof (center left); the bottom plan view showing slightly indented apex (lower right); the side elevation with flesh exposed showing slight red tint in yellow meat (lower left); and a stone and foliage typical of the new variety of nectarine tree.

DETAILED DESCRIPTION

Referring more specifically to the pomological details of the new and distinct variety of nectarine tree, unless otherwide stated, the following has been observed on 5 year old trees grown under the ecological conditions prevailing at the orchard of origin located in Eastern Fresno County near the town of Sanger. All major color code designations are by reference to the Dictionary of Color, by Maerz and Paul, Second Edition, 1950. Common color names are also occasionally employed.

Tree: Generally, eventual tree form and density are determined by the training system used in the orchard. The subject orchard has been trained using the standard 'open vase' system. The test orchard was propagated on 'Nemagard' peach rootstock.

*Size*.—Variable. Ranges from 3.3 m to 3.9 m in height and from 3.6 m to 4.2 m in width.

*Vigor*.—Vigorous. Reaches mature height of 3.9 m in 5 years. Annual renewal shoots at tree top average 1.3m in length.

*Shape*.—Upright to upright-spreading.

*Productivity*.—Very productive. Average production in fifth growing season is 99.5 kg per tree.

*Regularity of bearing*.—The tree consistently produces an abundance of flower buds resulting in high fruit sets and heavy, consistent yields, under typical Central San Joaquin Valley climatic conditions.

*Winter hardiness*.—The tree has not been exposed to freeze conditions in the geographic test area and winter hardiness is unknown.

Trunk:

*Size*.—Medium. The trunk circumference averaged 64 cm when measured 25 cm above the soil surface on 7 year old trees.

*Surface texture*.—Rough in bark texture. The bark surface is moderately scaly with a moderate amount of scarfskin present.

*Bark color*.—Grey-brown (7-A-9).

*Lenticels*.—Numerous bark lenticels are present, medium in size. The average width is 6 mm to 8 mm, and the average height is 3 mm to 4 mm.

*Lenticel color*.—(12-G-7, Pablo).

Primary branches:

*Size*.—The circumference average is 33 cm when measured 20 cm from the trunk on 7 year old trees.

*Surface texture*.—Rough.

*Bark color*.—(6-F-10, Aragon).

*Lenticels*.—Numerous bark lenticels are present, medium in size. They measure 6 mm to 8 mm in width and 3 mm to 4 mm in height.

*Lenticel color*.—(12-G-7, Pablo).

Leaves:

*Size*.—Generally — medium to large. Leaf measurements are from mature leaves growing near the midpoint of actively growing upright shoots.

*Average length*.—16 cm to 18 cm including the leaf petiole.

*Average width*.—3.5 cm to 4.5 cm.

*Leaf shape*.—Lanceolate.

*Apex shape*.—Acuminate.

*Venation*.—Pinnately net veined.

*Base shape*.—Cuneate.

*Color*.—Upper surface — 22-L-11), Paradise Green); under surface — (21-K-10).

*Marginal form*.—Finely serrate.

Glandular characteristics:

*Stem glands*.—Reinform in shape, 2 to 4 (mostly 2 to 3) located very near the stem junction with the leaf blade margin.

*Stem gland size*.—Length variable from 1 mm to 1.5 mm; Width 1 mm.

*Stem gland color*.—(15-L-6, Metallic green).

*Leaf blade glands*.—Reniform in shape, 0 to 3 (mostly 1) located at the base of the leaf blade.

*Leaf blade gland size*.—Length 1.5 mm; Width 1 mm.

*Leaf blade gland color*.—(20-K-5, Verdant Green).

Petiole:

*Length*.—10 mm to 12 mm.

*Thickness*.—2 mm.

*Stipules*.—None.

*Petiole color*.—(12-L-2, Chartreuse Green, Olive Yellow).

Flower:

*Flower buds*.—Dormant flower buds are medium to large in size and conic in shape, with short to medium pubescence on the sepals. The average length of the bud is 6 mm and the average diameter is 6 mm when measured on 15th November.

*Dormant bud color*.—(55-A-1).

*Flower bud chilling requirement*.—700 hours below 45° F.

Bloom:

*Bloom date*.—The average first bloom date is 2nd March and full bloom is 8th March near Sanger in the San Joaquin Valley of Central California.

*Bloom quality*.—Abundant. The flowers are numerous and vary from 0 to 2 (mostly 1 to 2) per node on fruiting shoots.

Flower characteristics:

*Flower size*.—Flowers are large and showy. Fully expanded flowers range from 40 mm to 45 mm in diameter.

*Petal size*.—Large. The average length is 20 mm. The average width is 18 mm.

*Petal quantity*.—Mostly 5 per flower.

*Petal shape*.—Ovate.

*Petal color*.—Upper surface (1-A-3, Peach Blossom). Lower surface (1-A-4).

*Flower pedicel size*.—Medium, ranging from 2 mm to 3 mm in length and averaging 1 mm in diameter.

*Flower pedicel color*.—(20-L-4).

*Sepal color*.—Upper surface (44-j-10).

*Stamen*.—Numerous, and variable in number (30 to 40 per flower).

*Filament length*.—Variable, 12 mm to 16 mm.

*Filament color*.—(1-A-1) on freshly opened flowers.

*Pistil quantity*.—One (rarely 2) per flower.

*Pistil length*.—Averages 17 mm (including ovary, style and stigma).

*Pistil color*.—(17-H-2) on freshly opened flowers.

*Pollen*.—Present in abundance.

*Pollen color*.—(4-I-11).

*Pollination requirement*.—Self-fertile.

Fruit: Maturity when described was the firm ripe condition typical of commercial harvest maturity. In 1997 the first harvest was on July 11, approximately 2 days later than 'Summer Fire' near Sanger in the San Joaquin Valley of Central California.

*Size*.—Generally large and uniform. Average diameter in the cheek plane is 70 mm to 72 mm. Average diameter transverse in the suture plane is 70 mm to 72 mm. Average diameter in the axial plane is 73 mm to 76 mm.

*Weight*.—During the 2000 harvest season observed weights of mature fruits ranged from 102 gm to 460 gm, with 88% of fruits ranging from 177 gm to 291 gm, and with 33% of fruits ranging from 235 gm to 255 gm.

*Shape*.—Most fruit symmetrical, some with sides unequal. Slightly oblong.

*Suture*.—Relatively shallow, inconspicuous line extending from base to apex, with a slight depression before and after the pistil point.

*Ventral surface*.—Smooth.

*Base*.—Shape is flat to slightly round.

*Apex*.—Shape is generally rounded.
*Pistil point*.—Shape is depressed.
*Fruit tendency to crack or split*.—None.
*Juice production*.—Juicy.
*Flavor*.—Sweet with slight acidity and well balanced.
*Amygdalin*.—Slight.
*Aroma*.—Pleasant and distinct.
*Flesh color*.—(9-L-6, Golden Glow); with some red streaks (5-L-1, Venetian Rose).
*Flesh texture*.—Firm and crisp. Numerous tough, course fibers are present within the flesh.
*Ripening*.—Evenly throughout.
*Brix*.—Soluble solids average 11.4%.
*Eating quality*.—Good.
*Use*.—Fresh market.
*Keeping quality*.—Excellent.
*Shipping and handling qualities*.—Excellent.
*Fruit*.—Brown Rot Tolerance: relatively low susceptibility when compared to 'Summer Fire' and 'July Red'.

Skin:
*Skin*.—Smooth, no pubescence.
*Color*.—Yellow with red overlay blush color (40 to 80% red over a yellow ground color).
*Blush color*.—Predominant blush color (4-L-12, Buccaneer) with some darker purple-red areas (7-L-, Algerian Red).
*Ground color*.—(9-L-6, Golden Glow).

Stem:
*Cavity shape*.—Acute. The average width is 24 mm, length is 24 mm and depth is 14 mm.
*Stem length*.—11 mm.
*Stem diameter*.—3 mm.
*Stem color*.—(18-L-2, Citronelle).

Stone:
*Attachment*.—Clingstone with long fibers.
*Size*.—Medium. The length is 40 mm; the width is 26 mm, and the thickness is 21.0 mm.
*Shape*.—Oblong. Base slightly flat to rounded; sides equally pitted, ridged near base.
*Apex shape*.—Acute.
*Color*.—(7-J-5, Tapestry Red).
*Ridges*.—Rounded.
*Grooves*.—Wide and shallow.
*Ventral edge*.—Thin throughout.
*Dorsal edge*.—Wide with a shallow groove.
*Cavity color*.—Generally the same as the skin ground color (9-L-6, Golden Glow), with a rough surface.
*Kernel*.—Length 20 mm; width 12 mm; thickness 3 mm.
*Kernel shape*.—Oblong, base slightly flat to rounded.
*Kernel apex shape*.—Acute.
*Kernel color*.—(15-A-12, Burnt Umber).
*Pit tendency to spilt*.—None.

Although the new variety of nectarine tree possesses the described characteristics noted above as a result of the growing conditions prevailing near Sanger in the Central part of the San Joaquin Valley of California, it is to be understood that variations of the usual magnitude and characteristics incident to changes in growing conditions, irrigation, fertilization, pruning, pest control, climatic variation and the like are to be expected.

I claim:

1. The new and distinct cultivar of nectarine plant, named 'Prima Diamond 19', as illustrated and described.

* * * * *